Figure 1:
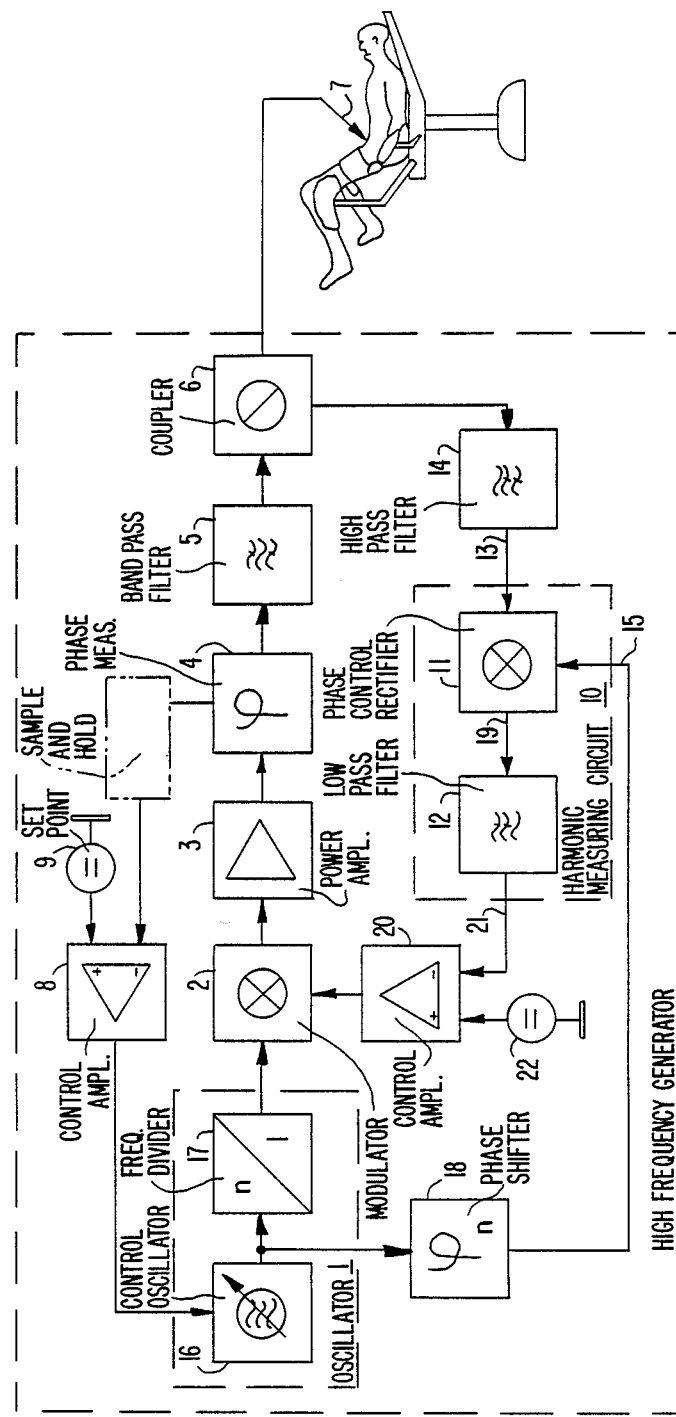

United States Patent [19]

Flachenecker et al.

[11] Patent Number: 4,818,954
[45] Date of Patent: Apr. 4, 1989

[54] HIGH-FREQUENCY GENERATOR WITH AUTOMATIC POWER-CONTROL FOR HIGH-FREQUENCY SURGERY

[75] Inventors: Gerhard Flachenecker, Ottobrunn; Karl Fastenmeier, Munich; Heinz Lindenmeier, Planegg, all of Fed. Rep. of Germany

[73] Assignee: Karl Storz Endoscopy-America, Inc., Culver City, Calif.

[21] Appl. No.: 11,781

[22] Filed: Feb. 6, 1987

[30] Foreign Application Priority Data

Feb. 15, 1986 [DE] Fed. Rep. of Germany ....... 3604823

[51] Int. Cl.$^4$ .......................... A61B 17/36; H03L 5/02
[52] U.S. Cl. ................................ 331/183; 128/303.14; 128/303.17; 128/422
[58] Field of Search .................... 331/183; 128/303.14, 128/303.17, 419 R, 422

[56] References Cited

U.S. PATENT DOCUMENTS

| | | | |
|---|---|---|---|
| 3,601,126 | 8/1971 | Estes | 128/303.14 |
| 3,875,945 | 4/1975 | Friedman | 128/303.14 |
| 4,114,623 | 9/1978 | Meinke et al. | 128/303.14 |
| 4,126,137 | 11/1978 | Archibald | 128/303.14 |
| 4,559,943 | 12/1985 | Bowers | 128/303.14 |

FOREIGN PATENT DOCUMENTS

| | | |
|---|---|---|
| 0058820 | 8/1986 | European Pat. Off. . |
| 2504280 | 8/1976 | Fed. Rep. of Germany . |
| 2931877 | 2/1981 | Fed. Rep. of Germany . |
| 3120102 | 12/1982 | Fed. Rep. of Germany . |
| 3119735 | 1/1983 | Fed. Rep. of Germany . |
| 3225222 | 1/1983 | Fed. Rep. of Germany . |
| 3225221 | 3/1983 | Fed. Rep. of Germany . |
| 3331896 | 3/1985 | Fed. Rep. of Germany . |
| 3510114 | 10/1985 | Fed. Rep. of Germany . |
| 3531576 | 5/1986 | Fed. Rep. of Germany . |

*Primary Examiner*—Siegfried H. Grimm
*Attorney, Agent, or Firm*—Donald D. Mon; David O'Reilly

[57] ABSTRACT

A high-frequency generator having automatic power-control for use in high-frequency surgery. The frequency of a high-frequency generator is adjustable by electronic circuit brought by a control circuit to a value such that at the output of the power amplifier there is an optimal phase relation between output voltage and output current, i.e., generally a phase shift of zero. The signal necessary for the control of the output power is obtained from harmonic oscillations generated by the arc at the surgical probe. A harmonic-measuring device to obtain the harmonic oscillations generated by the arc at the surgical probe has a phase-controlled rectifier which is controlled by the oscillator of the high-frequency generator. A simple filter is used at the output of the power amplifier, and the measurement filter used before the harmonic-measuring device can either be completely eliminated or need only be very simple in construction. No complicated filter adjustment is necessary and the power generator operates under optimal conditions and exhibits enhanced operating reliability.

14 Claims, 4 Drawing Sheets

HIGH-FREQUENCY GENERATOR WITH AUTOMATIC POWER-CONTROL FOR HIGH-FREQUENCY SURGERY

SUMMARY OF THE PATENT APPLICATION

The invention relates to a high-frequency generator with automatic power-control for high-frequency surgery. The frequency of the high-frequency generator is adjustable by electronic means and is brought by a control circuit to a value such that at the output of the power amplifier there is the optimal phase relation between output voltage and output current, i.e., generally the phase shift of zero. The signal necessary for the control of the output power is obtained from the harmonic oscillations generated by the arc at the surgical probe. Used for that purpose is a harmonic-measuring device with a phase-controlled rectifier which is controlled by the oscillator of the high-frequency generator. The advantage of the invention consists in the fact that a simple filter can be used at the output of the power amplifier, and the measurement filter before the harmonic-measuring device can either be completely eliminated or need only have a very simple construction. A complicated filter adjustment is not necessary. Nonetheless, the power generator operates under optimal conditions and exhibits enhanced operating reliability.

The invention relates to a high-frequency generator with automatic power-control for high-frequency surgery.

High-frequency currents are used in surgery for the cutting of human tissue when an especially bloodless incision is desired or when the operating site is not accessible with a normal scalpel but presents an access for a thin instrument through natural body openings such as the esophagus, intestines or urethra. Examples are the removal of prostatic adenomas, bladder tumors or intestinal polyps. In such cases, the high-frequency current is fed by a surgical probe into the tissue to be cut. The resulting dissipated heat causes boiling and vaporization of the cell fluid at this point, whereupon the cell walls tear open and the tissue is separated. The frequency of the utilized current must be above ca. 300 kHz in order not to trigger in the patient's body any electrochemical reactions of a magnitude such that an irritation of nerves or muscles occurs.

A problem in high-frequency surgery is the correct metering of the high-frequency generator's power. The power needed to cut human tissue depends on very many factors such as the cutting speed, dimensions and wearing of the surgical probe, condition of and blood flow through the tissue to be cut, presence and composition of a flushing liquid, etc. These factors may vary very markedly during a single incision, i.e., within approximately one second, and of course most certainly during an entire operation. If the power falls below the value necessary at any instant, the result is at least a deficient quality of the incision, or the surgical probe allows no further cutting at all. With manually adjustable high-frequency generators the physician must therefore select a power level that is still just adequate for the largest power requirement that occurs. This is an adjustment made from experience, which means a power excess during most of the operating time. This power excess is consumed in the form of an intense arc between the operation probe and the tissue being cut. This results in serious disadvantages of high-frequency surgery. An intense arc produces on the incision surface an excessive necrosis, which delays healing. Furthermore, an arc has a rectifying effect on the high-frequency current between fluid-containing tissue and a metallic probe. The resulting low-frequency currents can trigger in the patient an irritation of nerves or muscles, which can lead to dangerous situations such as "saltation" by the patient.

For this reason attempts have been made to automate the power output of the high-frequency generator and continuously to regulate the high-frequency generator to the smallest possible value of the output power. A device for the cutting and/or coagulating of human tissue with high-frequency current is known from German Patent No. 25 04 280. This device exploits the knowledge that, in principle, for the cutting of tissue a small arc is necessary between the surgical probe and the tissue in order—with the smallest possible total current—to make the current density in the tissue to be cut as large as possible. The arc should be as small as possible so as to keep the undesired side effects as small as possible, i.e., in general negligibly small. In German Patent No. 25 04 280 it is therefore proposed that the intensity of the arc be measured and that the measurement signal be used to regulate it to a constant value. In one version, the nonlinear action of the arc is used for that purpose. If the surgical probe is fed with a high-frequency voltage of one frequency, the arc generates currents at multiples of the generator frequency and in the region of zero frequency. These newly arising frequencies are called "harmonic frequencies" or the "harmonics" of the generator frequency. The amplitudes of these additional currents depend on the intensity of the arc. If one measures the amplitudes of the harmonics, one has a measure for the intensity of the arc and can use this measurement result to keep the intensity of the arc constant via a power control. If one regulates the intensity of the arc to a very small value, one has simultaneously attained the smallest possible output power of the high-frequency generator.

Here it should be noted that the amplitudes of the harmonics generated by the arc are very much smaller than the amplitude of the fundamental oscillation generated by the high-frequency generator at the generator frequency. Moreover, every high-frequency generator itself also generates harmonic frequencies besides the actual generator frequency. This is attributable to the nonlinearities of all known amplifier elements. In order not to interfere with the measurement of the harmonics generated by the arc, the harmonics generated by the generator must be very carefully filtered out. In German Patent No. 25 04 280 it is therefore proposed that between the high-frequency generator and the surgical probe there be placed an output filter which passes the currents of the generator frequency and blocks the currents of the harmonic frequencies, the harmonics being measured at the output gate of this filter facing away from the generator. Moreover, in order that the high voltages and currents at the generator frequency not interfere with the process of measuring the harmonics, it is proposed that before the measuring device used to measure the harmonics there be connected a measurement filter which blocks the generator frequency and passes only the harmonic frequencies.

These requirements result in a complicated system of filters whose dimensioning is very difficult, because other special features of the circuit have to be taken into account.

During high-frequency surgery the physician must not have his freedom of movement restricted by the high-frequency generator and electric leads to the surgical probe. For this reason the lead from the high-frequency generator to the surgical probe is usually very long and also laid in a loose and complicated manner. The return lead from the so-called neutral electrode (i.e. patient plate) to the generator is likewise usually very long. This results in leakage inductances and leakage capacitances which vary from operation to operation, but also during an operation. These reactive elements can detune the filter circuits described in German Patent No. 25 04 280.

The impedance which the patient presents to the high-frequency generator continues to vary constantly during the operation. By means of extensive measurements the inventors have ascertained that, for example, during transurethral prostate and bladder operations with high-frequency currents, impedances of between ca. 50 and 5000 ohms occur, with a concentration in the very broad range between 200 and 1000 ohms. With such sharply fluctuating patient impedances, filter dimensioning remains possible only if compromises are made.

The high blocking attenuation for the harmonics in the output filter with simultaneous low attenuation of the generator frequency, called for in German Patent No. 25 04 280, is achievable in practice only with a damping pole at the most strongly represented third harmonic. Likewise, the called-for high blocking attenuation of the measurement filter at the generator frequency is achievable only with a damping pole. This means that the high-frequency generator must operate at a fixed generator-frequency to which the filters are tuned.

In the design of the high-frequency generator, leakage inductances and leakage capacitances can be allowed for not at all or only with a mean value, and any change in these parasitic elements during operation leads to a mismatching of the reactive components of the patient's impedance. This results in restrictions on the available generator-power and again, of course, in detuning of the filters. In addition, the high-frequency generator operates, with a detuning, on a complex impedance. With all known amplifier circuits this results in problems with the dissipated power in the amplifier elements and, especially with switching amplifiers—which are used to achieve a high efficiency—leads to current and voltage overshoots during switching. This can interfere with the operating behavior of the high-frequency generator to the extent that it becomes unreliable and may fail due to destruction of an amplifier element. To alleviate these difficulties, the described filters must be of a multi-section filter design, which leads both to an increase of the transition loss, i.e., to a reduction of the efficiency, and to a decrease of the minimal blocking attenuation, i.e., to a deterioration of the arc's detection.

It is therefore the task of the invention to create a high-frequency generator with automatic power-control for high-frequency surgery in which the output filter has the simplest possible design, the measurement filter is either completely avoided or else also has the simplest possible design, both filters are uncritical with respect to fluctuations of the generator frequency, and fluctuations of the reactive component of the patient's impedance and/or of the parasitic reactive elements in the leads to the patient have no influence on the available power and on the operating behavior of the high-frequency generator.

Used as an oscillator is a circuit whose oscillation frequency is adjustable by electronic means. Thus, there is an intentional deviation from a fixed frequency as used in the prior art. At the output of the power amplifier there is connected a phase-measuring device which measures the phase shift between output voltage and output current of the power amplifier. The output signal of the phase-measuring device is fed back via a first control amplifier to the frequency control input of the oscillator in such a manner that the oscillator frequency changes until the phase shift between output voltage and output current of the power amplifier assumes a determined, preset value. This value for the phase shift between output voltage and output current corresponds to the optimal value at which the power amplifier encounters optimal operating conditions for power output, stability and possibly low distortion. In most cases, this value for the phase shift will be zero. The power amplifier then operates on a real load.

This frequency readjustment achieves the result that changes of the external parasitic elements such as lead inductances and lead capacitances, as well as tolerances of the frequency-determining elements in the output filter and variations of the values of components due to aging, have no influence on the behavior of the power amplifier. Because the power amplifier always operates on the impedance with the optimal phase relation between output voltage and output current, the power output and stability are optimal. At the same time, interfering effects such as voltage overshoots and switching under current flow in switching amplifiers are minimized, whereby the invention exhibits the further advantage of a substantially increased operating reliability.

In comparison to the prior art, the variable generator-frequency also makes inventive measures necessary in the branch for measuring the arc intensity, which means here for measuring the magnitude of the harmonic oscillations generated by the arc. As described in the assessment of the prior art, the control signal has been generated hitherto by rectifying one or more harmonic oscillations. Since the amplitudes of the harmonic oscillations are very much smaller than the amplitude of the fundamental oscillation generated by the power amplifier, according to the prior art a filter is connected before the harmonic-measuring device in order to suppress the generator frequency. The required high blocking attenuation can then be reached only with a damping pole at the generator frequency. However, with a variable oscillator-frequency this solution is no longer useable. Therefore, with a high-frequency generator according to the invention there is used as harmonic-measuring device a phase-controlled rectifier whose control signal is derived from the instantaneous frequency of the oscillator and which rectifies only one of the harmonics contained at the output of the high-frequency generator. The resulting output signal is fed to the modulator via a second control amplifier in such a way that the resulting instantaneous output power generates an arc of exactly prescribed intensity at the operation site. Here the phase-controlled rectifier simultaneously assumes the role of an adaptive filter which to a high degree suppresses all spectral components not to be rectified, hence also the generator frequency.

In an advantageous embodiment of the invention a band-pass filter is used as output filter. This band-pass filter is so dimensioned that all generator frequencies that occur in practice lie within its cut-off frequencies, whereas the higher harmonic to be rectified lies above the upper cut-off frequency. This requirement shall be explained with an example. A high-frequency generator built by the inventors has a nominal generator-frequency of 400 kHz. In very many tests it was found that in practical operation the generator frequency is regulated back and forth by the phase-measuring device within a frequency range of from 390 kHz to 410 kHz. The output filter was therefore provided with a pass range of from 380 kHz to 420 kHz so as also to provide adequate reserves for the case of component aging. The third harmonic was chosen as the harmonic to be rectified, because it exhibits the largest amplitude, hence produces the signal with the largest signal-to-noise ratio. Accordingly, the lowest frequency of the third harmonic lies at 1140 kHz. At this frequency the implemented output filter already has an attenuation of 52 dB, which is completely adequate to suppress the harmonic frequencies generated in the generator.

A low-pass filter can also be used as output filter. In this case, the cut-off frequency of the low-pass filter is to be so chosen that the highest occurring generator frequency lies below this cut-off frequency, whereas the higher harmonic to be rectified lies above it.

The arc between the surgical probe and the tissue acts like a current source for generating currents of harmonic frequencies. The measurement signal used to determine the intensity of the arc can therefore be obtained directly from the current in the patient circuit or, after a conversion, via a voltage measurement. In one embodiment of the invention the output impedance of the output filter is so designed as to be a high impedance at the harmonic frequency to be rectified. The arc-generated current of the relevant harmonic frequency then generates across the output impedance of the high-frequency generator a corresponding voltage of this frequency, which is fed to the harmonic-measuring device directly or via coupling elements. Such coupling elements can be, for example, coupling capacitors, transformers, resistive or capacitive voltage-dividers or phase shifters for phase correction of the measurement signal.

In another embodiment of the invention, the arc-generated current of the harmonic frequency is itself used to determine the arc intensity. For that purpose, the output filter is so designed that at its output terminals it has a low resistance for the harmonics to be rectified. In this case, the arc-generated current of the harmonic frequency can flow unimpeded in the patient circuit and via the output terminals of the high-frequency generator. By means of a coupling element, a measurement signal is coupled out from this circuit and fed to the harmonic-measuring device. For example, a low-resistance resistor or a transformer connected as a current transformer can be used here as coupling element.

In principle, a phase-controlled rectifier acts as a band-pass filter with very narrow bandwidth. The bandwidth can be kept arbitrarily small with a low-pass filter connected after the phase-controlled rectifier. For this reason, if this low-pass filter is suitably dimensioned, no measurement filter is necessary before the phase-controlled rectifier, since any arbitrary attenuation can be adjusted for all remote interference frequencies, hence especially the generator frequency. However, circuits are known and integrated circuits are available which operate excellently with low interference levels but fail when the interference amplitudes at the input of the circuit exceed certain values. The output voltage of a high-frequency generator for high-frequency surgery can be up to 1000 V, the output current up to 2 A. These are quite extreme interference signals for the phase-controlled rectifier, and can be controlled only with expensive, extremely linear special circuits that can be driven to high levels. To be sure, such circuits are familiar to the person skilled in the art, but require a large outlay for circuitry. Therefore, in another embodiment of the invention a measurement filter to suppress the generator frequency is connected before the input of the harmonic-measuring device. This measurement filter need not have a very high attenuation for the generator frequency, since it is intended to restrict only the dynamic range of the interference. In particular, it requires no damping pole at the generator frequency and thus does not restrict the use of a variable generator-frequency. The measurement filter is therefore very much simpler to dimension than in the case of the prior art.

In one embodiment of the invention there is used as measurement filter a band-pass filter whose cut-off frequencies include all frequencies that the harmonic to be rectified can assume. If one assumes equal reserves in the dimensioning, with the frequencies of the above example it would be necessary to choose a pass range of from 1140 kHz to 1260 kHz. Even a first-degree filter would then have an attenuation of ca. 26 dB at the generator frequency, which generally suffices as preattenuation of the interference for the phase-controlled rectifier.

Because of the filter characteristic of the phase-controlled rectifier, it is not absolutely necessary for the measurement filter to filter out the other harmonics not intended for rectification. Therefore, in another embodiment of the invention there is used as measurement filter a high-pass filter whose cut-off frequency lies between the highest occurring fundamental oscillation and the lowest occurring harmonic intended for rectification. This measurement filter thus again serves only as an overload protection against an inadmissible driving of the phase-controlled rectifier by the generator frequency.

Phase-controlled rectifiers evaluate the phase shift between the control voltage and the voltage to be measured. At a fully determined phase shift they output a maximal voltage which corresponds to the amplitude of the voltage to be rectified. For most circuits of phase-controlled rectifiers this phase shift is zero degrees. However, circuits are also known for which the necessary phase shift is 90 degrees. If the phase relation between the control voltage and the voltage to be measured differs from this phase relation, then the phase-controlled rectifier outputs a smaller voltage, usually described by a cosine function. In order really to measure the amplitude of the harmonic to be rectified, the control voltage and the measurement voltage must have this correct phase relation to each other. Now, the harmonic to be rectified may suffer phase shifts along the measurement branch. If, for example, the harmonic to be rectified is derived from the output voltage of the high-frequency generator, then said voltage is formed across the output impedance of the output filter. Because this filter generally has an imaginary output impedance at the frequency of the harmonic to be rectified, the result here is a phase shift of 90 degrees. A further phase shift can occur in a measurement filter that may be used. Therefore, in one embodiment of the invention, before the control input of the phase-controlled rectifier there is connected a phase shifter with which the optimal phase shift can be set between the control voltage and the measurement voltage. In another embodiment of the invention, before the measurement input of the phase-controlled rectifier there is connected a phase shifter with which likewise the optimal phase shift can be set between the control voltage and the measurement voltage.

In another embodiment of the invention, a quadrature demodulator is used as phase-controlled rectifier. This demodulator can be built, for example, in accordance with known rules from two phase-controlled rectifiers which are controlled with two orthogonal control voltages, i.e., control voltages phase-shifted by 90 degrees. The result is that the quadrature demodulator supplies two signals, A1 and A2, which, with the aid of the relation $$A = \sqrt{A1^2 + A2^2}$$

or in accordance with other laws that reflect this relation with adequate exactness, are combined to form the actual amplitude A of the harmonic to be rectified. Circuits which produce such a signal combination are known to a person skilled in the art. The signal A, which now has no dependence on the phase relation of the harmonic to be measured, is fed to the second control amplifier and used to control the output power of the high-frequency generator. A person skilled in the art is familiar with yet other circuits which, independently of the phase relation of the measurement voltage with respect to the control voltage, supply an output signal proportional to the amplitude of the harmonic to be rectified. These circuits can also be used in a high-frequency generator according to the invention.

In high frequency surgery, high-frequency generators are always operated with only a short duty cycle. A cutting generally lasts between approximately one and five seconds. Then, preparing for the next incision takes at least a few seconds. In order that the control loop used to set the generator frequency not have to set the optimal generator-frequency from arbitrary starting conditions at the beginning of each cut, in another embodiment of the invention a sample-and-hold amplifier is connected between the phase-measuring device and the first control amplifier. This sample-and-hold amplifier is so connected that it relays the present output signal of the phase-measuring device to the first control amplifier only when the generator has been activated by the physician. As soon as the generator is switched off by the physician, the sample-and-hold amplifier is driven into the hold status and, until the beginning of the next activation of the generator, continuously relays to the first control amplifier the last signal emitted by the phase-measuring device during an activation phase of the generator. In this way, the high-frequency generator, each time it is activated, can start with the best possible estimated value for the optimal frequency.

Many high-frequency generators for high-frequency surgery also have a coagulation mode for staunching bleeding that occurs during the high-frequency incision. In the coagulation mode the high-frequency power is not sent to the patient continuously but in short high-frequency pulses. These high-frequency pulses can be very short, i.e., only a few high-frequency periods long. In particular, the duration of such a high-frequency pulse can be so short that the frequency control loop cannot complete its transient period within this time. Therefore, in another embodiment of the invention the sample-and-hold amplifier is left in the hold status even during the generator activations in the coagulation mode, and the last signal emitted by the phase-measuring device during an incision activation of the high-frequency generator is continuously relayed to the first control amplifier. Thus, during the coagulation phases the high-frequency generator operates at a frequency that was determined to be optimal by the frequency control during the incision.

The arc between the surgical probe and the tissue to be cut is an alternating-current arc. For reasons of symmetry, mainly odd harmonics are generated by such an arc. Only for a higher intensity of the arc, which is supposed to be prevented by the power control, do the different work-functions and temperatures of the surgical probe and tissue result in fairly distinct asymmetries, which also lead to even harmonics, including the zero frequency. In any case, however, the amplitudes of the harmonics decrease with increasing order. For this reason, the third harmonic is present with the largest amplitude and is used in an advantageous version to rectify and thereby obtain the signal for controlling the power.

Figure 2:
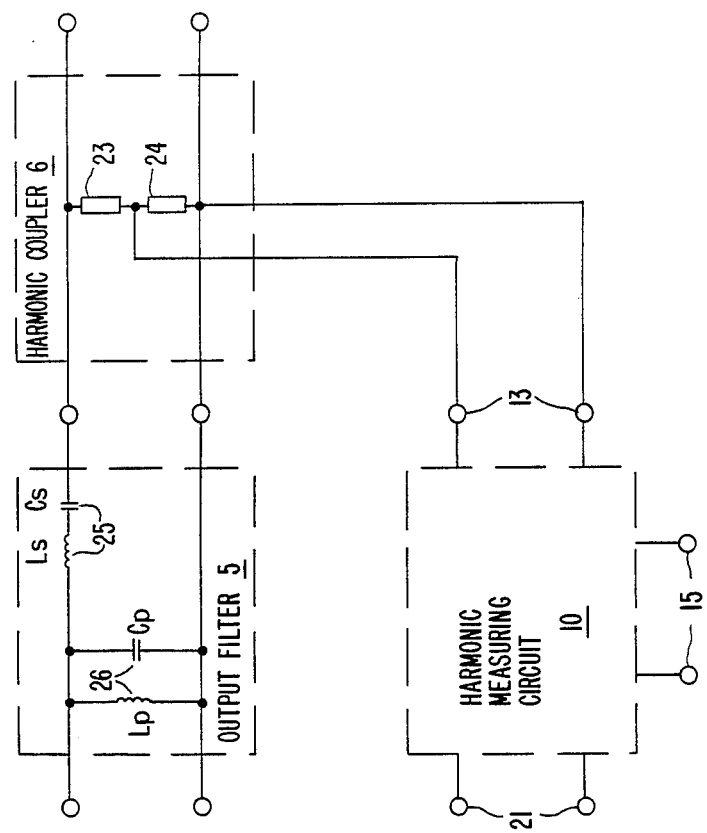
Figure 3:
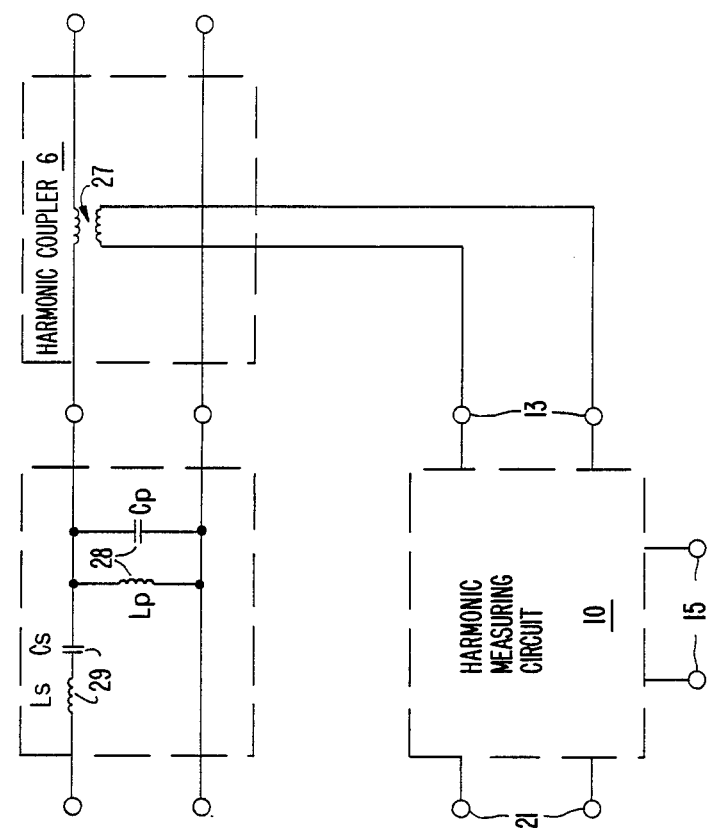
Figure 4:
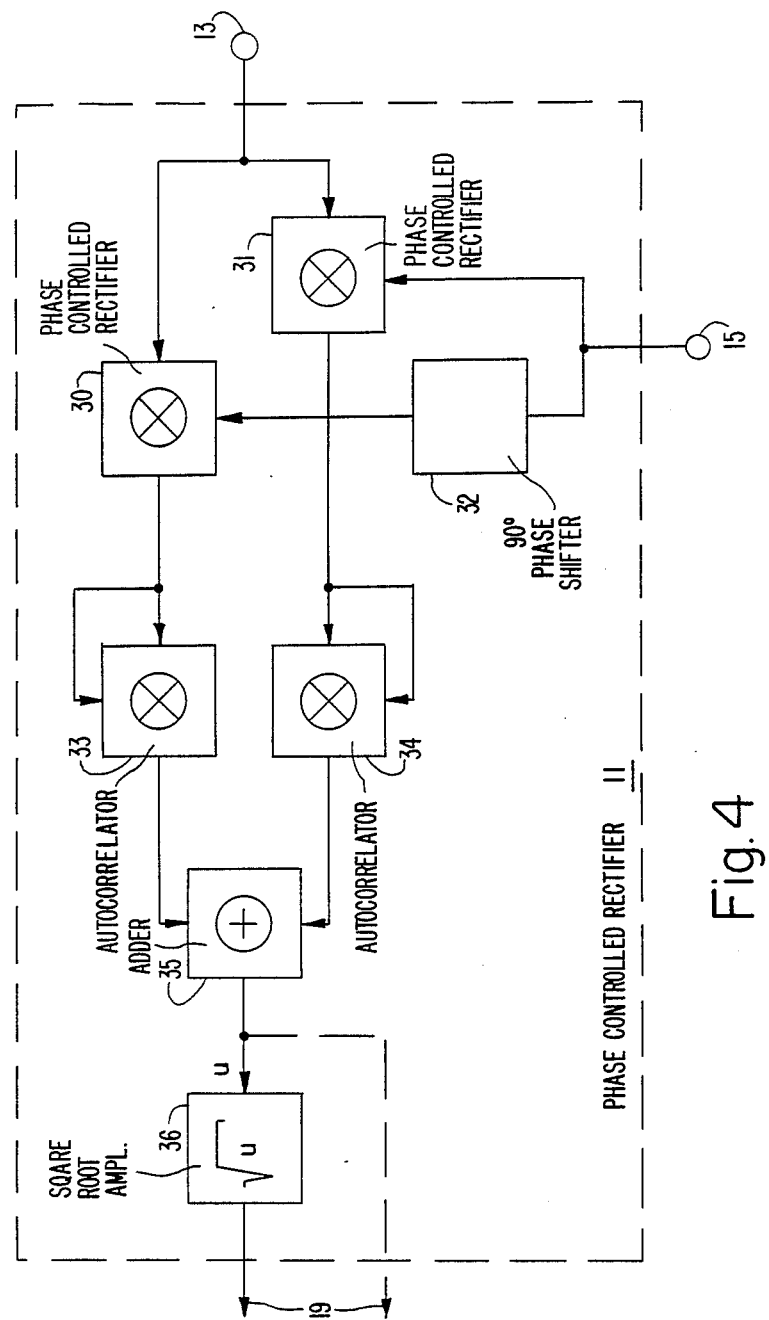

Figures are appended to clarify the invention.
Shown are:
FIG. 1: Block diagram of a high-frequency generator according to the invention.
FIG. 2: Example of a coupling out of the voltage of the harmonic at the output of the output filter.
FIG. 3: Example of a coupling out of the current of the harmonic at the output of the output filter.
FIG. 4: Implementation of a quadrature demodulator for phase-independent determination of the amplitude A of a harmonic.

FIG. 1 shows the block diagram of a high-frequency generator according to the invention. The oscillator 1 feeds a modulator 2 with the aid of which the amplitude of the output voltage and/or the output power can be controlled. At the output of the power amplifier 3 is the phase-measuring device 4, which measures the phase shift between the output voltage and the output current of the power amplifier. Following the phase-measuring device 4 are the output filter 5 and a device 6 for coupling-out the harmonic. Finally comes the surgical probe 7.

It is not absolutely necessary that, as indicated in this example, the phase-measuring device pick off both the output voltage and the output current directly after the power amplifier. If, for example, the output filter is designed as a band-pass filter and the first element consists of a series-resonant circuit, then the current even after this first element of the filter is identical to the output current of the power amplifier. In this case, the current signal for the phase-measuring device can also be taken from the filter itself. Thus it should be made clear that the here-described sequence of the individual components is to be understood as an example and can vary in practice without departing from the idea of the invention.

The output signal of the phase-measuring device 4 is fed back via the first control amplifier 8 to the oscillator 1. Here the output signal of the phase-measuring device 4 is compared with a setpoint value 9, which is so chosen that it corresponds to the optimal phase-value. This value is usually zero.

The signal coupled-out with the coupling elements 6 is fed to the harmonic-measuring device 10. The harmonic-measuring device 10 contains a phase-controlled rectifier 11 and a low-pass filter 12, the latter serving to adjust the measurement bandwidth. In control engineering, the low-pass filter 12 is also called a loop filter, because it determines the frequency response of the control loop, here the power-control loop. To achieve optimal power-control response, this loop filter 12 has to be dimensioned in accordance with complicated rules, which are, however, known to a person skilled in the art. It can be stated, though, that here the loop filter in principle has a low-pass response.

In this exemplary embodiment, before the measurement input 13 of the phase-controlled rectifier there is connected a measurement filter 14, which in this example is a high-pass filter. The high-pass filter 14 is so dimensioned that its cut-off frequency lies between the highest occurring generator frequency and the lowest occurring harmonic frequency to be rectified. It attenuates the generator frequency contained in the measurement signal of the phase-controlled rectifier to such an extent that the linearity range of the phase-controlled rectifier is not exceeded. Thus, for example, a commercially available integrated circuit with a small linearity range can be used as phase-controlled rectifier. If the phase-controlled rectifier with large linearity range were suitably dimensioned, the measurement filter 14 would not be necessary.

The control signal, which is derived from the oscillator oscillation, is fed to the phase-controlled rectifier 11 at its control input 15. The control signal and the harmonic to be rectified must have the same frequency and a fixed phase with respect to each other, a phase dependent on the operating principle of the phase-controlled rectifier. In this exemplary embodiment the frequency of the control voltage is formed by using in the oscillator 1 a control oscillator 16 which oscillates at n times the generator frequency, where n is the order of the harmonic to be rectified. If, for example, the third harmonic is to be rectified, then n=3 and the control oscillator 16 oscillates at three times the generator frequency. Here the control voltage for the phase-controlled rectifier 11 is picked off directly from the control oscillator 16, while the generator frequency is formed by a frequency divider 17 with the division ratio n:1. The output signal of the frequency divider 17 represents the actual oscillator oscillation.

A phase shifter 18 is connected before the control input 15 of the phase-controlled rectifier 11. Its phase shift at n times the generator frequency is so adjusted that the control voltage at the control input 15 and the harmonic to be rectified at the measurement input 13 of the phase-controlled rectifier 11 have exactly the mutual phase shift for which the phase-controlled rectifier 11 supplies the maximal output signal.

After passing through the loop filter 12, the output signal 19 of the phase-controlled rectifier 11 is fed to the second control amplifier 20 as input signal 21. The control amplifier 20 compares the signal 21 with a setpoint value 22 with which the momentarily desired intensity of the arc at the surgical probe 7 can be preselected. The output signal of the second control amplifier 20 is finally fed to the modulator 2, which sets the necessary output power of the high-frequency generator.

Illustrated in FIG. 2 is an example of the derivation of the harmonic to be rectified from the output voltage of the high-frequency generator. The voltage divider formed from the resistors 23 and 24 is used for that purpose. In the generation of the harmonic the arc at the surgical probe 7 acts as a current source. In order for a voltage to be obtained from the current of the harmonic to be rectified, the output impedance of the output filter 5 must be a high impedance at the harmonic frequency to be rectified. In the exemplary embodiment per FIG. 2, this condition is met with the indicated circuit of a band-pass filter for the generator frequency. The series-resonant circuit 25 formed from Ls and Cs has its series, resonance at the nominal generator-frequency and is a high impedance at all harmonic frequencies.

The depicted circuit is to be understood only as an example. The band-pass filter formed from the resonant circuits 25 and 26 can also be executed in other circuit variants in accordance with known rules, so long as the output impedance of the output filter 5 meets the condition of high resistance at the harmonic to be rectified. The band-pass filter can also contain transformers, especially if the power amplifier is designed as a push-pull amplifier.

FIG. 3 shows a circuit in which the harmonic to be rectified is derived from the output current of the high-frequency generator. For that purpose, a transformer 27 connected as a current transformer is used in one of the output leads of the high-frequency generator. In this case, the current of the harmonic frequency to be rectified, generated by the arc at the surgical probe 7, must be able to flow unhindered in the output circuit of the high-frequency generator. This condition is met in the indicated exemplary embodiment with the parallel-resonant circuit 28, which is a constituent of the band-pass filter consisting of resonant circuits 28 and 29, which filter is tuned to the generator frequency. This circuit, too, is to be understood only as an example.

The example of a block diagram for a quadrature demodulator is indicated in FIG. 4. The measurement signal fed to the measurement input 13, which signal contains the harmonic to be rectified, is fed simultaneously to the measurement inputs of the two phase-controlled rectifiers 30 and 31. The control signal applied at the control input 15 is fed unchanged to the control input of the one phase-controlled rectifier 31 and phase-shifted by 90 degrees to that of the other. Two orthogonal components of the harmonic to be rectified are thereby produced at the outputs of the phase-controlled rectifiers. These two signals are squared in the autocorrelators 33 and 34 and are added in the addition element 35. The resulting output signal 19 corresponds to the square of the amplitude of the harmonic to be rectified. Even this signal can be further processed as a control signal, as can be seen in FIG. 4 with the dashed output-line, since the control task is only to keep constant the amplitude of the harmonic to be rectified. Here, of course, it also suffices to keep constant the square of this amplitude. Then only the square of this amplitude, which is also a measure for the arc intensity, has to be adjusted as setpoint value 22. If the nonlinearity of the setpoint value 22 resulting herefrom is undesired, or if stability problems arise because of the nonlinearity of the control loop, then the signal can still be further processed via a square-root amplifier 36, as indicated in FIG. 4.

The advantage of a quadrature demodulator is its independence of phase changes of the measurement voltage. Quadrature demodulators which act according to the scheme described in FIG. 4 or operate according to other principles are available as integrated circuits. When an integrated circuit is used, it is of course necessary to be aware of the modulation range and, in general, to use a measurement filter, as disclosed in the idea of the invention.

We claim:

1. High-frequency generator with automatic power-control for high-frequency surgery, consisting of an oscillator for generating the generator frequency, a modulator for controlling the output amplitude, a power amplifier for generating the necessary high-frequency power, an output filter for suppressing frequencies other than the generator frequency of the high-frequency generator, and a harmonic-measuring device for measuring the amplitude of a selected harmonic frequency of the generator frequency in the output circuit of the high-frequency generator, said selected harmonic frequency being generated by the arc existing between the surgical probe and the tissue to be cut during the cutting process, characterized in that
    (a) the frequency of the oscillator (1) is adjustable by electronic means,
    (b) at the output of the power amplifier (3) there is a phase-measuring device (4) which measures the phase shift between the output voltage and output current of the power-amplifier (3),
    (c) the output signal of the phase-measuring device (4) is fed back by means of a first control amplifier (8) to a frequency-control input of the oscillator (I) in such a way that the phase shift between the output voltage and output current of the power amplifier (3) at the thus adjusted frequency corresponds to the ideal value for the power amplifier (3), of generally approximately zero degrees, and
    (d) the harmonic-measuring device (10) contains a phase-controlled rectifier (11) whose control signal is derived from the instantaneous frequency of the oscillator (I) and which rectifies only said selected harmonic frequency of the harmonic frequencies contained in the frequency mixture at the output of the high-frequency generator, and the output signal of the harmonic-measuring device (10) is fed to the modulator (2) via a second control amplifier (20) as control signal for controlling the output power of the high-frequency generator.

2. High-frequency generator with automatic power-control for high-frequency surgery in accordance with claim 1, characterized in that the output filter (5) is a band-pass filter whose upper and lower cut-off frequencies are so dimensioned that all generator frequencies occurring during operation lie between these cut-off frequencies, whereas the harmonic frequency to be rectified lies above the upper cut-off frequency.

3. High-frequency generator with automatic power-control for high-frequency surgery in accordance with claim 1, characterized in that
    the output filter (5) is a low-pass filter whose cut-off frequency is so dimensioned that all generator frequencies occurring during operation lie below this cut-off frequency, whereas the harmonic frequency to be rectified lies above the cut-off frequency.

4. High-frequency generator with automatic power-control for high-frequency surgery in accordance with claims 1, 2 or 3 characterized in that the output impedance of the output filter (5) is a high impedance at the harmonic frequency to be rectified, and that the signal fed to the harmonic-measuring device (10) is derived from the output voltage of the high-frequency generator.

5. High-frequency generator with automatic power-control for high-frequency surgery in accordance with claims 1, 2 or 3, characterized in that the output impedance of the output filter (5) is of low impedance at the harmonic frequency to be rectifier, and that the signal fed to the harmonic-measuring device (10) is derived from the output current of the high-frequency generator.

6. High-frequency generator with automatic power-control for high-frequency surgery in accordance with claim 5, characterized in that
    before the harmonic-measuring device (10) there is connected a measurement filter (14) for suppressing the generator frequency, the attenuation of which filter at all occurring generator frequencies is so high that the linearity range of the phase-controlled rectifier (11) is not exceeded by the measurement signal.

7. High-frequency generator with automatic power-control for high-frequency surgery in accordance with claim 6, characterized in that the measurement filter (14) is a bandpass filter whose upper and lower cut-off frequencies are so dimensioned that the harmonic frequency to be rectified lies between these cut-off frequencies for all generator frequencies occurring during operation, whereas the generator frequency lies below the lower cut-off frequency.

8. High-frequency generator with automatic power-control for high-frequency surgery in accordance with claim 6, characterized in that
    the measurement filter (14) is a high-pass filter whose cut-off frequency is so dimensioned that the harmonic frequency to be rectified lies above this cut-off frequency for all generator frequencies occurring during operation, whereas the generator frequency lies below it.

9. High-frequency generator with automatic power-control for high frequency surgery in accordance with claim 8, characterized in that before the measurement input (13) of the phase-controlled rectifier (11) there is connected a phase shifter (18) which at the frequency of the harmonic to be rectified has a phase shift such that after the phase shifter the harmonic generated by the arc has the phase relation required by the phase-controlled rectifier (11), relative to the control voltage at the control input (15) of the phase-controlled rectifier (11), said control voltage being derived from the oscillator.

10. High-frequency generator with automatic power-control for high-frequency surgery in accordance with claim 8, characterized in that
    before the control input (15) of the phase-controlled rectifier (11) there is connected a phase shifter (18) which at the frequency of the harmonic to be rectified has a phase shift such that after the phase shifter (18) the control voltage derived from the oscillator (1) has the phase relation required by the phase-controlled rectifier (11), relative to the arc-generated harmonic at the measurement input (13) of the phase-controlled rectifier (11).

11. High-frequency generator with automatic power-control for high-frequency surgery in accordance with claim 8, characterized in that
as phase-controlled rectifier (11) there is used a quadrature demodulator whose output signal with an arbitrary phase relation between the control signal (15) and the measurement signal (13) corresponds to the amplitude of the harmonic to be rectified.

12. High-frequency generator with automatic power-control for high-frequency surgery in accordance with claim 11, characterized in that
between the phase-measuring device (4) and the first control amplifier (8) there is connected a sample-and-hold amplifier which relays the signal emitted by the phase-measuring device to the first control amplifier only when the high-frequency generator has been activated and which is driven into the hold status when the high-frequency generator is not activated, whereupon it then maintains the last signal emitted by the phase-measuring device during an activation phase of the high-frequency generator.

13. High-frequency generator with automatic power-control for high-frequency surgery in accordance with claim 11, characterized in that
between the phase-measuring device (4) and the first control amplifier (8) there is connected a sample-and-hold amplifier which relays the signal emitted by the phase-measuring device to the first control amplifier only when the high-frequency generator is activated in the cutting mode and which is driven into the hold status when the high-frequency generator is in the coagulation mode or is not activated at all, whereupon it then maintains the last signal emitted by the phase-measuring device during an activation phase of the high-frequency generator in the cutting mode.

14. High-frequency generator with automatic power control for high-frequency surgery in accordance with claim 13, characterized in that
said selected harmonic frequency to be rectified is three times the generator frequency.

* * * * *